US012734116B2

(12) United States Patent
Deng et al.

(10) Patent No.: US 12,734,116 B2
(45) Date of Patent: Sep. 15, 2026

(54) CATIONIC MATERIAL FOR TOOTH DESENSITIZATION, PREPARATION METHOD THEREFOR, AND APPLICATION THEREOF

(71) Applicants: PEKING UNIVERSITY SCHOOL AND HOSPITAL OF STOMATOLOGY, Beijing (CN); BEIJING PIEZO-DENT MEDICAL TECHNOLOGY CO., LTD., Beijing (CN)

(72) Inventors: Xuliang Deng, Beijing City (CN); Yan Wei, Beijing City (CN); Xuehui Zhang, Beijing City (CN); Xinyu Liu, Beijing City (CN); Nuo Chen, Beijing City (CN); Jingjing Deng, Beijing City (CN); Shengjie Jiang, Beijing City (CN)

(73) Assignees: PEKING UNIVERSITY SCHOOL AND HOSPITAL OF STOMATOLOGY, Beijing (CN); BEIJING PIEZO-DENT MEDICAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 18/835,951

(22) PCT Filed: Sep. 5, 2022

(86) PCT No.: PCT/CN2022/117054

§ 371 (c)(1),
(2) Date: Aug. 5, 2024

(87) PCT Pub. No.: WO2023/173700

PCT Pub. Date: Sep. 21, 2023

(65) Prior Publication Data

US 2025/0143980 A1 May 8, 2025

(30) Foreign Application Priority Data

Mar. 15, 2022 (CN) ......................... 202210266168.1
Jun. 29, 2022 (CN) ......................... 202210758648.X

(51) Int. Cl.

| | |
|---|---|
| ***A61K 8/04*** | (2006.01) |
| ***A61K 8/41*** | (2006.01) |
| ***A61K 8/65*** | (2006.01) |
| ***A61K 8/73*** | (2006.01) |
| ***A61K 8/81*** | (2006.01) |
| ***A61Q 11/00*** | (2006.01) |

(52) U.S. Cl.
CPC .............. *A61K 8/042* (2013.01); *A61K 8/416* (2013.01); *A61K 8/65* (2013.01); *A61K 8/731* (2013.01); *A61K 8/8129* (2013.01); *A61K 8/8147* (2013.01); *A61Q 11/00* (2013.01)

(58) Field of Classification Search
CPC ........ A61K 8/8129; A61K 8/731; A61K 8/65; A61K 31/715; A61K 8/042; A61K 8/416; A61K 6/20; A61K 8/8147; A61K 2300/00; A61Q 11/00
See application file for complete search history.

(56) References Cited

U.S. PATENT DOCUMENTS 5,270,031 A 12/1993 Lim et al.

FOREIGN PATENT DOCUMENTS

| | | | | |
|---|---|---|---|---|
| CN | 105007987 A | | 10/2015 | |
| CN | 108794736 A | | 11/2018 | |
| CN | 110755297 A | | 2/2020 | |
| CN | 114469989 A | | 5/2022 | |
| CN | 114948988 A | | 8/2022 | |
| EP | 2476406 A2 | | 7/2012 | |
| WO | 2004041228 A1 | | 5/2004 | |
| WO | WO-2005092271 A1 | * | 10/2005 | ........... A61K 9/7053 |
| WO | 2016078831 A | | 5/2016 | |
| WO | WO-2016078831 A1 | * | 5/2016 | ............ A61K 8/442 |

OTHER PUBLICATIONS

International Search Report issued in International Application No. PCT/CN2022/117054; mailed Dec. 16, 2022; 7 pgs.
First Office Action issued in Chinese Application No. 202210758648.X; mailed Jul. 6, 2023; 13 pgs.
Second Office Action issued in Chinese Application No. 202210758648.X; mailed Oct. 13, 2023; 13 pgs.
Notification of Grant Patent Right for Invention issued in CN Patent Application No. 202210758648.X; mailed Nov. 29, 2023; 3 pages.

* cited by examiner

*Primary Examiner* — Lezah Roberts
(74) *Attorney, Agent, or Firm* — HAUPTMAN HAM, LLP

(57) ABSTRACT

The present invention relates to a cationic material for tooth desensitization, a preparation method therefor, and an application thereof, for use in solving the technical problems in the prior art of long time consumption and limited treatment effect of materials for dentin hypersensitivity. The cationic material comprises a main chain skeleton polymer and a cationic group derived on the main chain skeleton polymer, and the main chain skeleton polymer is connected to the cationic group by means of a covalent bond. The present invention can be used for preparing a drug for treating the dentin hypersensitivity.

5 Claims, 9 Drawing Sheets

Hydroxyethyl cellulose + 2,3-Epoxypropyltrimethylammonium chloride $\xrightarrow{OH^-}$ Cationized hydroxyethyl cellulose (polyquaternium-10)
FIG. 1A
Chitosan — Methacrylic anhydride, 60 °C, 6 h ⟹ Methacrylated chitosan
FIG. 1B
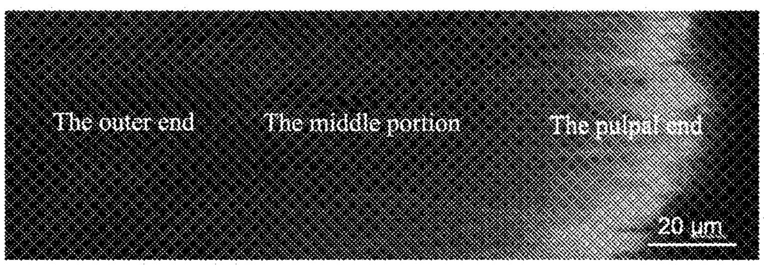
FIG. 2A
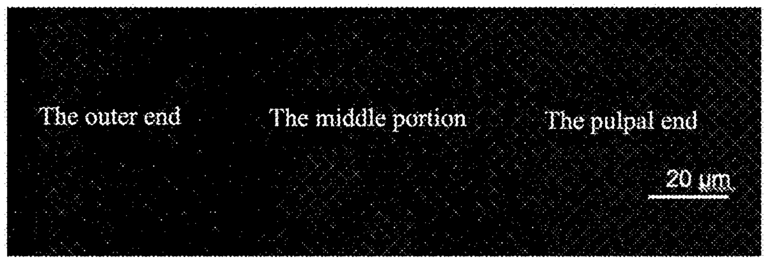
FIG. 2B

CATIONIC MATERIAL FOR TOOTH DESENSITIZATION, PREPARATION METHOD THEREFOR, AND APPLICATION THEREOF

RELATED APPLICATIONS

The present application is a U.S. National Phase of International Application Number PCT/CN2022/117054 filed Sep. 5, 2022, which claims priority to Chinese Application Number 202210266168.1, filed Mar. 15, 2022, and Chinese Application No. 202210758648.X, filed Jun. 29, 2022.

TECHNICAL FIELD

The present disclosure relates to a dental material, a preparation method therefor, and application thereof, in particular to a cationic material for tooth desensitization, a preparation method therefor, and application thereof.

BACKGROUND

Dentin hypersensitivity is a short, sharp pain arising from exposed dentin in response to external stimuli typically thermal, evaporative, mechanical, or chemical, and which cannot be ascribed to any dental defect or disease due to any other specific causes. Currently, the most widely accepted mechanism of dentin hypersensitivity is the hydrodynamic theory. That is, when dentin is exposed, various external temperature changes, mechanical stimuli, or chemical stimuli acting on the surface of the exposed dentinal tubules cause changes in the flow of dentinal tubule fluid—either an increase in quantity or a change in direction, and such abnormal flow transmits to the dental pulp, causing excitation of nerve fibers and the sensation of pain.

At present, the treatments for dentin hypersensitivity mainly include desensitizing toothpaste containing various ingredients, fluoride-containing desensitizing mouthwash, resin adhesives, fluoride-coated desensitizing drugs, Gluma desensitizer, and also laser therapy applied to desensitization treatment. According to what has been reported in the literature, the effectiveness of various desensitization methods commonly used in current clinical practice varies. For the use of desensitizing toothpaste, the immediate effectiveness ranges from 15.7% to 31.1%, and the 3-month effectiveness ranges from 54.9% to 85.2%. For the use of laser sealing, the immediate effectiveness ranges from 88.7% to 94%, and the 3-month effectiveness ranges from 58% to 83%. For the use of a resin adhesive, the immediate effectiveness ranges from 62.3% to 73%, and the 3-month effectiveness ranges from 65% to 77%.

Moreover, using the above substances as treatments for dentin hypersensitivity means complex and time-consuming processes, and the treatment outcomes are often limited. In addition, in clinical practice, patients often continue to experience varying levels of dentin hypersensitivity symptoms.

SUMMARY

Aiming to address the technical problems in the prior art, that is, long treatment duration and limited treatment effectiveness in the treatments for dentin hypersensitivity with the mentioned materials, the present disclosure provides a cationic material with a good desensitization effect, a preparation method therefor, and application thereof.

To achieve this object, the present disclosure provides a cationic material for tooth desensitization, which comprises a main chain skeleton polymer and a cationic group derived on the main chain skeleton polymer, wherein the main chain skeleton polymer is connected to the cationic group by means of a covalent bond; the main chain skeleton polymer is one or more of polysaccharides, synthetic polymers, or proteins in any combination; and the cationic group is one or more of primary amines, primary amine salts, secondary amines, secondary amine salts, tertiary amines, tertiary amine salts, quaternary amines, quaternary amine salts, piperidinium, pyrrolidine, imidazolium, and pyridinium in any combination.

Preferably, the polysaccharides include one or more of hydroxyethyl cellulose, hydroxypropyl cellulose, carboxymethyl cellulose, hyaluronic acid, chitosan, alginate, lignin, dextran, soluble starch, and polysaccharide; the synthetic polymers include one or more of polyethylene glycol, branched polyethylene glycol, polyvinyl alcohol, a block copolymer of polyoxyethylene-polyoxypropylene ether, dimethyl diallyl ammonium chloride, carbomer, poly(methyl)acrylates, poly(methyl)acrylamides, polyethyleneimine, and polyamino acid; and the proteins include one or more of gelatin, collagen, elastin, elastin-like polypeptides, silk fibroin, serum albumin, casein, soy protein, mucin, fibrin, and polynucleotide.

Preferably, the cationic material for tooth desensitization is a solution of polyquaternium-10 hydrogel with a mass concentration of 0.1% to 10%; and the polyquaternium-10 has a molecular weight of 100 to 5,000 kDa, a charge density of 0.0001 to 0.002 eq/g, and a nitrogen content of 0.5 to 2.5 wt %.

The present disclosure provides a preparation method for a cationic material for tooth desensitization, comprising the following steps: (1) dispersing, in deionized water, one or more of hydroxyethyl cellulose, hydroxypropyl cellulose, carboxymethyl cellulose, hyaluronic acid, alginate, lignin, dextran, soluble starch, polysaccharide, polyethylene glycol, branched polyethylene glycol, polyvinyl alcohol, a block copolymer of polyoxyethylene-polyoxypropylene ether, dimethyl diallyl ammonium chloride, carbomer, poly(methyl)acrylates, poly(methyl)acrylamides, polyethyleneimine, polyamino acid, gelatin, collagen, elastin, elastin-like polypeptides, silk fibroin, serum albumin, casein, soy protein, mucin, fibrin, and polynucleotide in any combination; stirring to dissolve the solute uniformly, and thereafter, respectively adding sodium hydroxide and a combined solution containing a modifier with one or more groups selected from primary amines, primary amine salts, secondary amines, secondary amine salts, tertiary amines, tertiary amine salts, quaternary amines, quaternary amine salts, piperidinium, pyrrolidine, imidazolium, and pyridinium; and letting them react; (2) neutralizing the reaction mixture obtained in the step (1) with hydrochloric acid, and then performing dialysis and freeze-drying to obtain a cationic material; and (3) preparing the cationic material obtained in the step (2) into a cationic material hydrogel solution with a mass concentration of 0.1% to 10%.

Preferably, in the step (1), the reaction is carried out with stirring at 30° C. to 95° C. for 0.5 to 24 hours; and in the step (3), the cationic material is slowly added into rapidly stirred deionized water, the temperature is raised to 30° C. to 95° C. to accelerate the swelling rate of the cationic material, and after 0.5 to 24 hours, a uniform and transparent solution is formed, so that the cationic hydrogel solution is prepared.

The present disclosure further provides use of the cationic material for tooth desensitization in the preparation of a drug for treating dentin hypersensitivity.

Preferably, in the use of the cationic material for tooth desensitization in the preparation of a drug for treating dentin hypersensitivity provided by the present disclosure, the cationic material for tooth desensitization is prepared into a cationic hydrogel material with a mass concentration of 0.01% to 10%.

Preferably, in the use of the cationic material for tooth desensitization in the preparation of a drug for treating dentin hypersensitivity provided by the present disclosure, the cationic material for tooth desensitization is prepared into toothpaste.

Preferably, in the use of the cationic material for tooth desensitization in the preparation of a drug for treating dentin hypersensitivity provided by the present disclosure, the cationic material for tooth desensitization is used to coat the surface of tooth coverings, and lastly, a backing film layer is affixed onto the cationic gel.

Preferably, in the use of the cationic material for tooth desensitization in the preparation of a drug for treating dentin hypersensitivity provided by the present disclosure, the tooth coverings include dental braces, dental adhesives, retainers, dental patches, and chewing gum; and the backing film layer is selected from one or more of EVA films, PLA films, and PVA films.

The present disclosure offers the following advantageous effects:

The cationic material for tooth desensitization provided by the present disclosure can effectively enter the dentinal tubules. Test results have demonstrated that the cationic material for tooth desensitization provided by the present disclosure could significantly reduce the increase in electrical current values caused by acid, base, cold, hot, and pressure stimuli, as well as markedly lower the action potentials produced in animal dentin hypersensitivity models. Moreover, clinical desensitization experiments have shown that the cationic material for tooth desensitization could effectively alleviate patients' pain, with treatment effectiveness reaching 85% to 95% or higher; besides, during the 3-month observation period, there was no significant decline in treatment effectiveness, which could remain at 85% to 90%. Compared with the desensitization methods commonly used in current clinical practice, such as desensitizing toothpaste, resin adhesives, fluoride, and laser, the cationic desensitizing material of the present disclosure offers advantages such as convenient clinical operation, long-lasting treatment effectiveness, and no damage to the affected teeth or patients.

BRIEF DESCRIPTION OF THE DRAWINGS

FIG. 1A illustrates the reaction formula for the preparation of polyquaternium-10, the main component of the cationic material for tooth desensitization in the present disclosure.

FIG. 1B illustrates the reaction formula for the preparation of CSMA hydrogel, the main component of the cationic material for tooth desensitization in the present disclosure.

FIGS. 2A and 2B are images acquired by laser scanning confocal microscopy showing the results obtained after treating dentinal tubules with a positively charged stain and a negatively charged stain in the present disclosure, wherein FIG. 2A shows the results of treating dentinal tubules with a positively charged stain, and FIG. 2B shows the results of treating dentinal tubules with a negatively charged stain.

FIGS. 3A, 3B, and 3C are respectively schematic diagrams of the sulfonated rhodamine stained-cationic hydrogel (polyquaternium-10 hydrogel) entering the interior of dentinal tubules, as observed through a laser scanning confocal microscope in the present disclosure, wherein FIG. 3A is a schematic diagram of the cationic hydrogel entering the tubules as observed in the sagittal plane; FIG. 3B is a schematic diagram of the cationic hydrogel entering the tubules as observed in the coronal plane; and FIG. 3C is a schematic diagram of the cationic hydrogel filling the dentinal tubules and blocking stimuli-induced cation migration.

FIGS. 5A, 5B, and 5C show the electrochemical test results of the dentin hypersensitivity model of an extracted tooth treated with the PQ-10 hydrogel, wherein FIG. 5A is a schematic diagram of the response currents measured under acid and base stimulation; FIG. 5B is a schematic diagram of the response currents measured under temperature stimulation; and FIG. 5C is a schematic diagram of the response currents measured under pressure stimulation.

FIGS. 5D, 5E, and 5F show the electrochemical test results of the dentin hypersensitivity model of a living animal treated with the PQ-10 hydrogel, wherein FIG. 5D is a schematic diagram of the response currents measured under acid and base stimulation; FIG. 5E is a schematic diagram of the response currents measured under temperature stimulation; and FIG. 5F is a schematic diagram of the response currents measured under pressure stimulation.

FIGS. 6A, 6B, and 6C show the electrochemical test results of the dentin hypersensitivity model of an extracted tooth treated with the CSMA hydrogel, wherein FIG. 6A is a schematic diagram of the response currents measured under acid and base stimulation; FIG. 6B is a schematic diagram of the response currents measured under temperature stimulation;

and FIG. 6C is a schematic diagram of the response currents measured under pressure stimulation.

FIGS. 6D, 6E, and 6F show the electrochemical test results of the dentin hypersensitivity model of a living animal treated with the CSMA hydrogel, wherein FIG. 6D is a schematic diagram of the response currents measured under acid and base stimulation; FIG. 6E is a schematic diagram of the response currents measured under temperature stimulation; and FIG. 6F is a schematic diagram of the response currents measured under pressure stimulation.

DETAILED DESCRIPTION

Figure 3A:
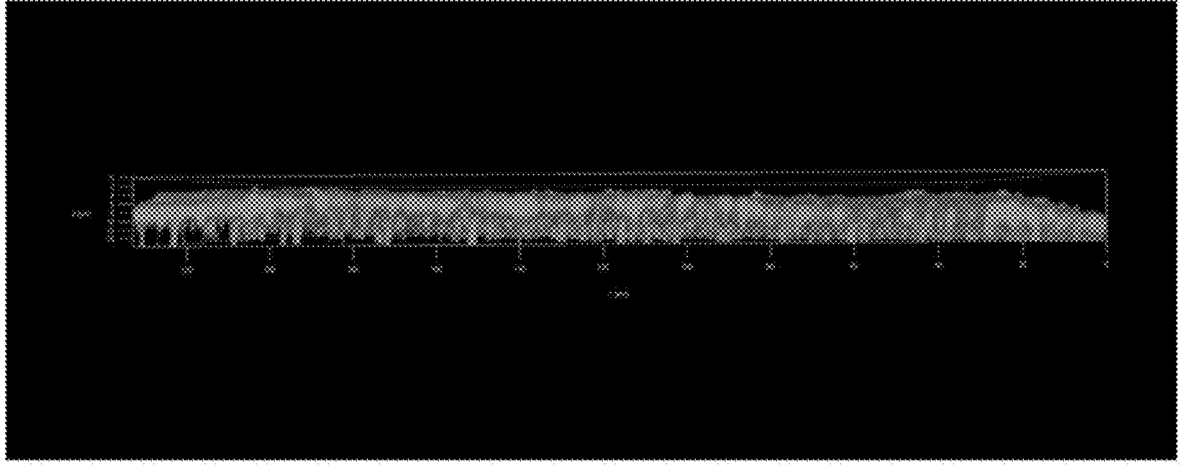

The present disclosure is further described below with reference to the following Examples.

Example 1

Characterization of electrical properties of the interior of the dentinal tubules. 5 mg of positively charged rhodamine-6 g powder was dissolved in 1 ml of deionized water, and the solution was placed in a constant temperature shaker at 25° C. and 300 r/min to work for 5 minutes in the dark to allow complete dissolution, resulting in a rhodamine-6 g stain. The dentin part of an extracted tooth was cut into slices about 1 mm thick each in the horizontal direction. An acid etchant containing 30% phosphoric acid was applied to the dentin slices. 30 seconds later, the acid etchant was rinsed with water for 15 seconds to remove the surface-contaminated layer. The rhodamine-6 g stain was applied on a treated dentin slice, and the slice was left to stand for 30 minutes in the dark. Then, the stained slice was rinsed with deionized water 5 times for 1 minute each time. Until the resulting rinse solution did not change color, a laser scanning confocal microscope was used to observe the slice. According to the result shown in FIG. 2A, the interior of the dentinal tubules exhibited visible staining, with the staining intensity gradually decreasing from the pulpal end to the outer end. This staining result indicated that the interior of the dentinal tubules was negatively charged, and the charge showed a gradually weakening trend from the pulpal end to the outer end. Similarly, 5 mg of negatively charged sulfonated rhodamine powder was dissolved in 1 ml of deionized water, and the solution was placed in a constant temperature shaker at 25° C. and 300 r/min to work for 5 minutes in the dark to allow complete dissolution, resulting in a sulfonated rhodamine stain. The sulfonated rhodamine stain was used to treat a dentinal tubule slice. The result observed through laser scanning confocal microscopy is shown in FIG. 2B. No staining was found in the dentinal tubules. This result suggested an asymmetric distribution of negative charge in the interior of the dentinal tubules.

Example 2

The present disclosure provided a cationic hydrogel, which is a solution of polyquaternium-10 hydrogel with a mass concentration of 3%. 30 mg of polyquaternium-10 powder (with a molecular weight of 450 kDa, a charge density of 0.0012 eq/g, and a nitrogen content of 1.85 wt %) was weighed and slowly added into 1 mL of deionized water under rapid stirring. The temperature was raised to 65° C. to accelerate the swelling rate of polyquaternium-10. After 1 hour, a uniform and transparent solution was formed, so that a solution of polyquaternium-10 hydrogel with a mass concentration of 3% was prepared. The sample was sterilized in an autoclave at 120° C. for 30 minutes and then stored in a refrigerator at 4° C. for later use.

Example 3

The present disclosure provided a cationic hydrogel, which is a solution of polyquaternium-10 hydrogel with a mass concentration of 0.1%. 10 mg of polyquaternium-10 powder (with a molecular weight of 100 kDa, a charge density of 0.002 eq/g, and a nitrogen content of 2.5 wt %) was weighed and slowly added into 1 mL of a phosphate buffer solution (with a molar concentration of 50 mM and a pH value of 8) under rapid stirring. The temperature was raised to 30° C. to accelerate the swelling rate of polyquaternium-10. After 0.5 hour, a uniform and transparent solution was formed, so that a solution of polyquaternium-10 hydrogel with a mass concentration of 0.1% was prepared. The sample was sterilized in an autoclave at 120° C. for 30 minutes and then stored in a refrigerator at 4° C. for later use.

Example 4

The present disclosure provided a cationic hydrogel, which is a solution of polyquaternium-10 hydrogel with a mass concentration of 10%, 50 mg of polyquaternium-10 powder (with a molecular weight of 2,000 kDa, a charge density of 0.0010 eq/g, and a nitrogen content of 1.5 wt %) was weighed and slowly added into 1 mL of a citrate buffer solution (with a molar concentration of 200 mM and a pH value of 5) under rapid stirring. The temperature was raised to 75° C. to accelerate the swelling rate of polyquaternium-10. After 5 hours, a uniform and transparent solution was formed, so that a solution of polyquaternium-10 hydrogel with a mass concentration of 10% was prepared. The sample was sterilized in an autoclave at 120° C. for 30 minutes and then stored in a refrigerator at 4° C. for later use.

Research findings indicated that the cationic hydrogel with a mass concentration of 0.1% had a weak effect on the generation of electric currents and action potentials in response to stimuli in its application, and the cationic hydrogel with a mass concentration of 3% had the best effect on the generation of electric currents and action potentials in response to stimuli in its application. Herein, the cationic hydrogel with a mass concentration of 3% was subsequently used for in vitro and in vivo experiments to verify the effectiveness of dentin hypersensitivity treatments.

Example 5

The present disclosure provided a preparation method for a cationic hydrogel, which comprises the following steps: (1) dispersing hydroxyethyl cellulose in deionized water, stirring to dissolve the solute uniformly, and thereafter, respectively adding sodium hydroxide and a 2,3-epoxypropyltrimethylammonium chloride solution, and letting them react; (2) neutralizing the reaction mixture obtained in the step (1) with hydrochloric acid, and then performing dialysis and freeze-drying to obtain cationized hydroxyethyl cellulose, i.e., polyquaternium-10; and (3) preparing the polyquaternium-10 obtained in the step (2) into a solution of polyquaternium-10 hydrogel with a mass concentration of 3%.

In the step (1), the reaction was carried out with stirring at 65° C. for 24 hours. In the step (2), the polyquaternium-10 had a molecular weight of 450 kDa, a charge density of 0.0012 eq/g, and a nitrogen content of 1.85 wt %. In the step (3), the polyquaternium-10 was slowly added into deionized water under rapid stirring; the temperature was raised to 65° C. to accelerate the swelling rate of polyquaternium-10; after 1 hour, a uniform and transparent solution was formed, so that a solution of polyquaternium-10 hydrogel was prepared.

Example 6

The present disclosure provided a cationic desensitizing hydrogel, based on the mechanism that the cations block the cation migration in dentinal tubules, as a desensitizing product for the treatment of dentin hypersensitivity. Methacrylated-modified chitosan (Synthesis of chitosan modified by methacrylic anhydride; CSMA) was used to prepare the hydrogel desensitizing product to verify the treatment effectiveness of the cationic hydrogel.

The CSMA hydrogel used in the present disclosure was prepared as follows: the CSMA conjugate was synthesized through a chemoselective one-step N-acetylation reaction between chitosan and methacrylic anhydride, wherein the chemical formula is shown in FIG. 1B. Specifically, methacrylic anhydride was added dropwise to a 1 wt. % acetic acid solution of chitosan, where the ratio of anhydride to amino group was 1:1. The reaction was carried out at 60° C. After being stirred for about 6 hours, the reaction solution was dialyzed in distilled water in the dark (the molecular weight cutoff of the dialysis bag was MW 3,500 Da) for about 3 days. After the resultant solution was freeze-dried, a sponge-like final product was obtained and stored at room temperature for later use.

The way to use the product: preparing the CSMA material into a hydrogel with a mass concentration of 10%, applying the desensitizing hydrogel on the exposed dentin surface of the hypersensitive tooth, and 5 minutes later, wiping off the excess hydrogel on the surface, thereby achieving the desensitizing treatment effect.

Example 7

The present disclosure provided a cationic desensitizing hydrogel and a preparation method therefor. Hydroxypropyl cellulose was dispersed in deionized water. The solution was stirred to dissolve the solute uniformly, and thereafter, required amounts of sodium hydroxide and a 2,3-epoxypropyltrimethylammonium chloride solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then it was freeze-dried and weighed to obtain cationized hydroxypropyl cellulose. 30 mg of the cationized hydroxypropyl cellulose powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 3% was prepared. The sample was sterilized in an autoclave at 120° C. for 30 minutes and then stored in a refrigerator at 4° C. for later use.

Example 8

The present disclosure provided a cationic desensitizing hydrogel and a preparation method therefor. Hydroxypropyl cellulose was dispersed in deionized water. The solution was stirred to dissolve the solute uniformly, and thereafter, required amounts of sodium hydroxide and a 2,3-epoxypropyldimethylamine solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then it was freeze-dried and weighed to obtain cationized hydroxypropyl cellulose. 30 mg of the cationized hydroxypropyl cellulose powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 3% was prepared. The sample was sterilized in an autoclave at 120° C. for 30 minutes and then stored in a refrigerator at 4° C. for later use.

Example 9

The present disclosure provided a cationic desensitizing hydrogel and a preparation method therefor. Hydroxypropyl cellulose was dispersed in deionized water. The solution was stirred to dissolve the solute uniformly, and thereafter, required amounts of sodium hydroxide and a 1-epoxypropyl-3-methylimidazolium chloride solution were respectively added, and then the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then it was freeze-dried and weighed to obtain cationized hydroxypropyl cellulose. 30 mg of the cationized hydroxypropyl cellulose powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 3% was prepared. The sample was sterilized in an autoclave at 120° C. for 30 minutes and then stored in a refrigerator at 4° C. for later use.

Example 10

The present disclosure provided a cationic desensitizing hydrogel and a preparation method therefor. Polyvinyl alcohol was dispersed in deionized water. The solution was stirred to dissolve the solute uniformly, and thereafter, required amounts of sodium hydroxide and a 2,3-epoxypropyltrimethylammonium chloride solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then it was freeze-dried and weighed to obtain cationized polyvinyl alcohol. 100 mg of the cationized polyvinyl alcohol powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 10% was prepared. The sample was sterilized in an autoclave at 120° C. for 30 minutes and then stored in a refrigerator at 4° C. for later use.

Example 11

The present disclosure provided a cationic desensitizing hydrogel and a preparation method therefor. Polyvinyl alcohol was dispersed in deionized water. The solution was stirred to dissolve the solute uniformly, and thereafter, required amounts of sodium hydroxide and a 2,3-epoxypropyldimethylamine solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then it was freeze-dried and weighed to obtain cationized polyvinyl alcohol. 100 mg of the cationized polyvinyl alcohol powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 10% was prepared. The sample was sterilized in an autoclave at 120° C. for 30 minutes and then stored in a refrigerator at 4° C. for later use.

Example 12

The present disclosure provided a cationic desensitizing hydrogel and a preparation method therefor. Polyvinyl alcohol was dispersed in deionized water. The solution was stirred to dissolve the solute uniformly, and thereafter, required amounts of sodium hydroxide and a 1-epoxypropyl-3-methylimidazolium chloride solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then it was freeze-dried and weighed to obtain cationized polyvinyl alcohol. 100 mg of the cationized polyvinyl alcohol powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 10% was prepared. The sample was sterilized in an autoclave at 120° C. for 30 minutes and then stored in a refrigerator at 4° C. for later use.

Example 13

The present disclosure provided a cationic desensitizing hydrogel and a preparation method therefor. Gelatin was dispersed in deionized water. The solution was stirred to dissolve the solute uniformly, and thereafter, required amounts of sodium hydroxide and a 2,3-epoxypropyltrimethylammonium chloride solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then it was freeze-dried and weighed to obtain cationized gelatin. 50 mg of the cationized gelatin powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 5% was prepared. The sample was sterilized in an autoclave at 120° C. for 30 minutes and then stored in a refrigerator at 4° C. for later use.

Example 14

The present disclosure provided a cationic desensitizing hydrogel and a preparation method therefor. Gelatin was dispersed in deionized water. The solution was stirred to dissolve the solute uniformly, and thereafter, required amounts of sodium hydroxide and a 2,3-epoxypropyldimethylamine solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then freeze-dried and weighed to obtain cationized gelatin. 50 mg of the cationized gelatin powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 5% was prepared. The sample was sterilized in an autoclave at 120° C. for 30 minutes and then stored in a refrigerator at 4° C. for later use.

Example 15

The present disclosure provided a cationic desensitizing hydrogel and a preparation method therefor. Gelatin was dispersed in deionized water. The solution was stirred to dissolve the solute uniformly, and thereafter, required amounts of sodium hydroxide and a 1-epoxypropyl-3-methylimidazolium chloride solution were respectively added. Then, the resultant solution was stirred and allowed to react for 24 hours at 65° C. Lastly, the reaction mixture was neutralized with hydrochloric acid; placed in deionized water and dialyzed with a 10 kDa dialysis bag for 3 days; and then freeze-dried and weighed to obtain cationized gelatin. 50 mg of the cationized gelatin powder was weighed and slowly added into 1 mL of deionized water under rapid stirring. The temperature was raised to 65° C. to accelerate the swelling rate. After 1 hour, a uniform and transparent solution was formed, so that a solution of hydrogel with a mass concentration of 5% was prepared. The sample was sterilized in an autoclave at 120° C. for 30 minutes and then stored in a refrigerator at 4° C. for later use.

Example 16

The present disclosure provided cationic desensitizing toothpaste as a desensitizing product for the treatment of dentin hypersensitivity, based on the mechanism that the cations block the cation migration in dentinal tubules. Any of the cationic materials obtained above was mixed with a toothpaste matrix at a mass ratio of 1:(10 to 1,000), wherein the matrix comprised abrasive(s) (25% to 60%), humectant (s), adhesive(s), foaming agent(s), sweetener(s) (0.01% to 0.1%), a certain volume of deionized water, preservative(s) and flavor(s). Flavor(s), active additive(s), stabilizer(s), and saccharin were dissolved to reach a uniform state in a pre-dissolving pot or pre-mixing pot, and then were added into a paste-making pot. The liquid materials in the liquid storage tank were separately measured and added to the paste-making pot, and powder materials were added thereafter. After the addition of the powder materials, flavors were added. The mixture was then subjected to stirring with a scraper, homogeneously stirring, and grinding. Next, the mixture was transferred into a paste storage pot for aging, which allowed the materials to naturally cool to room temperature while fully expanding to form a homogeneous adhesive body to improve the elasticity thereof. The aging time was about 120 minutes. The way to use the product: using it while brushing your teeth by applying a small amount of the toothpaste on the exposed dentin surface of the hypersensitive teeth; 10 minutes later, brushing off the toothpaste, thereby achieving a desensitizing treatment effect.

Example 17

The present disclosure provided cationic desensitizing dental braces as a desensitizing product for the treatment of dentin hypersensitivity, based on the mechanism that the cations block the cation migration in dentinal tubules. The tissue surface of dental braces was coated with any of the cationic hydrogels obtained above with a coating thickness of 100 μm, and then the hydrogel coating was covered with a tissue surface backing film (PVA film) to obtain a desensitizing product for treating dentin hypersensitivity, based on the mechanism that the cations block the cation migration in dentinal tubules.

The way to use the product: after peeling off the backing film (PVA film) of the dental braces, putting the dental braces into the mouth so that the tissue surface with the cationic gel comes into contact with the exposed dentin surface of the hypersensitive teeth; and after 1 hour, a desensitizing treatment effect will be achieved.

Example 18

The present disclosure provided a cationic desensitizing dental adhesive as a desensitizing product for the treatment of dentin hypersensitivity, based on the mechanism that the cations block the cation migration in dentinal tubules. The surface of the dental adhesive was coated with any of the cationic materials obtained above with a coating thickness of 300 μm, and then the hydrogel coating was covered with a backing film (PLA film) to obtain a desensitizing product for treating dentin hypersensitivity, based on the mechanism that the cations block the cation migration in dentinal tubules.

The way to use the product: after peeling off the backing film (PVA film) of the dental adhesive, letting the cationic gel come into contact with the exposed dentin surface of the hypersensitive teeth; and after 2 hours, a desensitizing treatment effect will be achieved.

Example 19

The present disclosure provided a cationic desensitizing retainer as a desensitizing product for the treatment of dentin hypersensitivity, based on the mechanism that the cations block the cation migration in dentinal tubules. The surface of the retainer was coated with any of the cationic gels obtained above with a coating thickness of 500 μm, and then the hydrogel coating was covered with a backing film (EVA film) to obtain a desensitizing product for treating dentin hypersensitivity, based on the mechanism that the cations block the cation migration in dentinal tubules.

The way to use the product: after peeling off the backing film (EVA film) of the retainer, letting the cationic gel come into contact with the exposed dentin surface of the hypersensitive teeth; and after 3 hours, a desensitizing treatment effect will be achieved.

Example 20

The present disclosure provided a cationic desensitizing dental patch as a desensitizing product for the treatment of dentin hypersensitivity, based on the mechanism that the cations block the cation migration in dentinal tubules. The tissue surface of the dental patch was coated with any of the cationic gels obtained above with a coating thickness of 10 μm, and then the hydrogel coating was covered with a backing film (PLA film) to obtain a desensitizing product for treating dentin hypersensitivity, based on the mechanism that the cations block the cation migration in dentinal tubules.

The way to use the product: after peeling off the backing film (PLA film) of the dental patch, letting the cationic gel come into contact with the exposed dentin surface of the hypersensitive teeth; and after 2 hours, a desensitizing treatment effect will be achieved.

Example 21

Figure 3B:
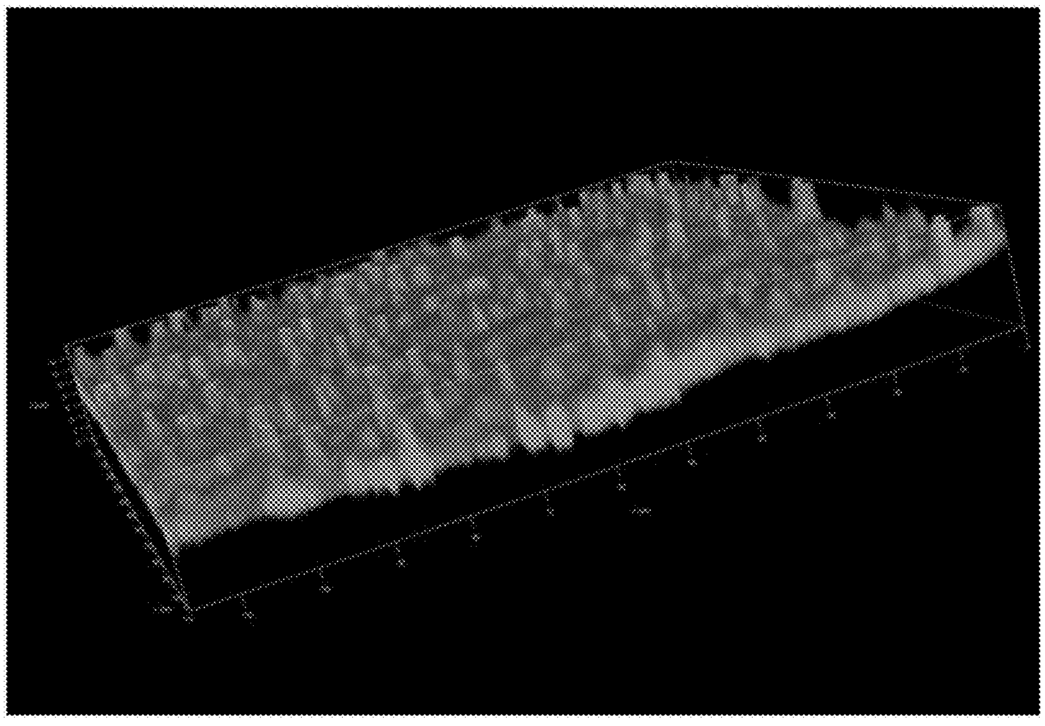
Figure 3C:
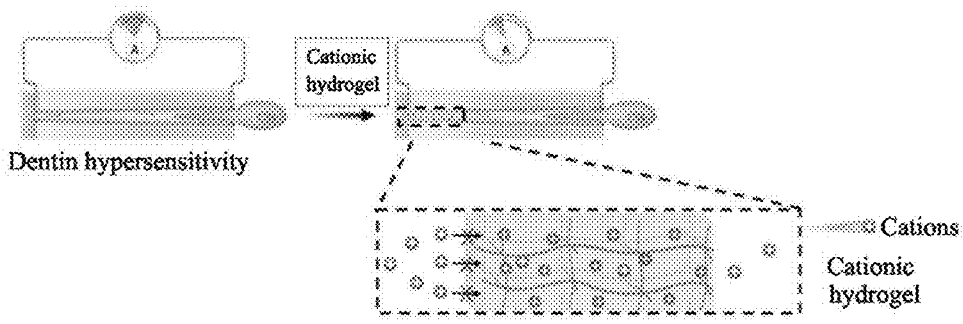
Figure 4:
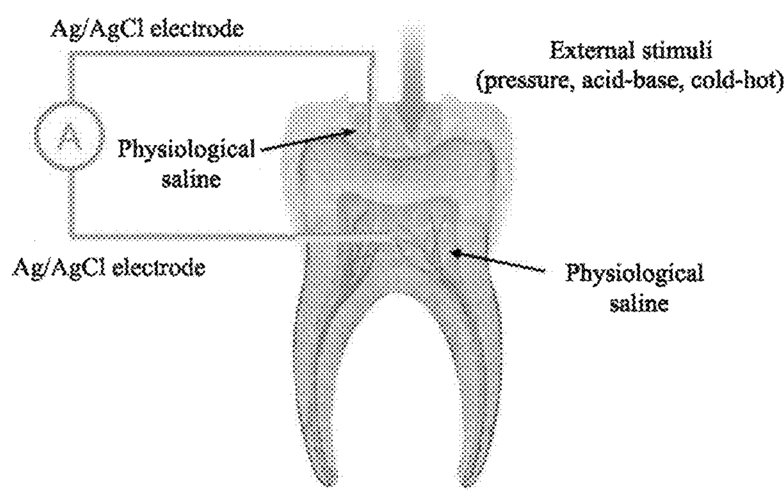
FIG. 4 is a schematic diagram of the construction of the dentin hypersensitivity model in the present disclosure.

The effectiveness of the cationic materials entering dentinal tubules was assessed as below. The PQ-10 cationic hydrogel and the CSMA cationic hydrogel prepared in Example 2 and Example 3 were used for assessing the entry of cationic materials into the dentinal tubules. 5 mg of a negatively charged sulfonated rhodamine powder was dissolved in 1 mL of gel and the solution was placed in a constant temperature shaker at 25° C. and 300 r/min to work for 5 minutes in the dark to allow complete dissolution. The dentin part of an extracted tooth was cut into slices about 1 mm thick each in the horizontal direction. An acid etchant containing 30% phosphoric acid was applied to the dentin slices. 30 seconds later, the acid etchant was rinsed with water for 15 seconds to remove the surface-contaminated layer. The stained cationic hydrogel was applied on a treated dentin slice, and the slice was left to stand for 5 minutes in the dark. Then, the slice was observed under a laser scanning confocal microscope. As shown in FIG. 3, within the observable range, the stained cationic hydrogel effectively entered the dentinal tubules. The schematic diagram is shown in FIG. 3C.

Example 22

Through electrochemical detection, the PQ-10 cationic hydrogel and the CSMA cationic hydrogel prepared in Example 2 and Example 3 were used to assess the desensitizing effects of the cationic materials on a dentin hypersensitivity model of an extracted tooth.

1) A dentin hypersensitivity model was constructed on an extracted tooth. Of the measurement electrodes of a picoammeter, the positive electrode was placed in an electrolytic cell, and the negative electrode was placed in the dental pulp chamber. Under an external voltage of 0 V, pressure stimuli (100, 200, 300, and 400 mmHg), acid-base stimuli (pH=5, 5.5, 6, 6.5, 7.5, 8, 8.5, and 9), and cold-hot stimuli (5° C., 13° C., 21° C., 29° C., 45° C., 53° C., 61° C., and 69° C.) were applied to the electrolyte solution (physiological saline) in the electrolytic cell, and the resulting changes in electric current on the hypersensitivity model were detected.

2) On the dentin hypersensitivity model of the extracted tooth, the value of the forward current induced by the strongest acid stimulus was approximately 43.06 nA, which decreased to 22.67 nA after the gel treatment. The value of the reverse current induced by the strongest base stimulus was approximately −19.53 nA, which decreased to −11.05 nA after the PQ-10 gel treatment.

3) On the dentin hypersensitivity model of the extracted tooth, the value of the forward current induced by the strongest cold stimulus was approximately 475.4 nA, which decreased to 207.25 nA after the gel treatment. The value of the reverse current induced by the strongest hot stimulus was approximately −425.2 nA, which decreased to −218.55 nA after the PQ-10 gel treatment.

4) On the dentin hypersensitivity model of the extracted tooth, the value of the forward current induced by the strongest pressure stimulus was approximately 28.36 nA, which decreased to 22.18 nA after the PQ-10 gel treatment.

Figures 5A, 5B, 5C:
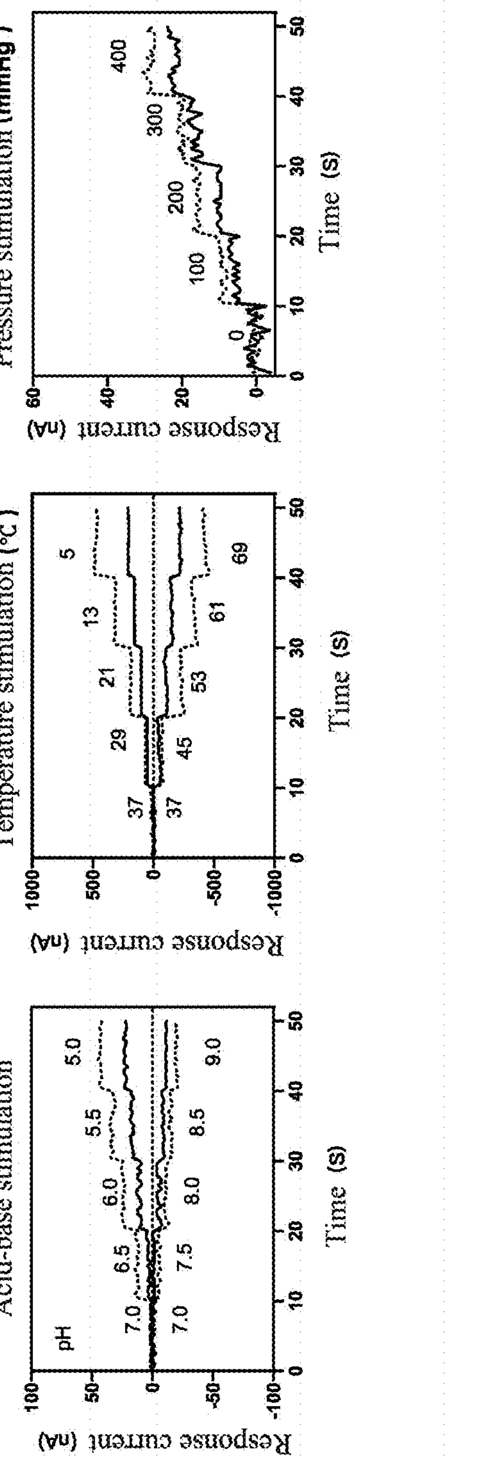

The results of the PQ-10 gel treatment on the extracted tooth are shown in FIGS. 5A, 5B, and 5C.

Figure 6C:
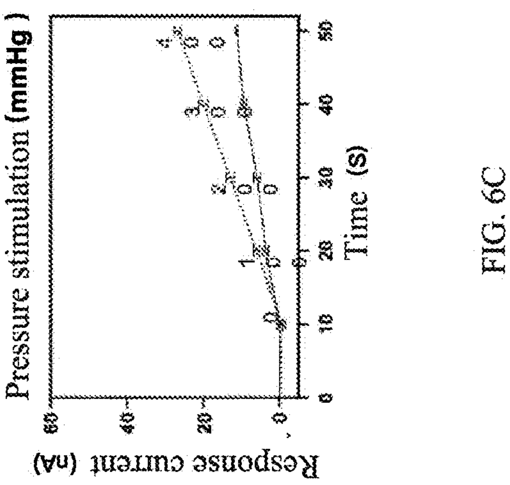
Figure 6B:
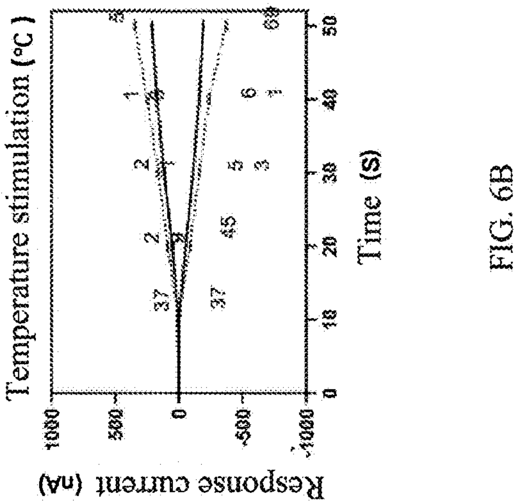
Figure 6A:
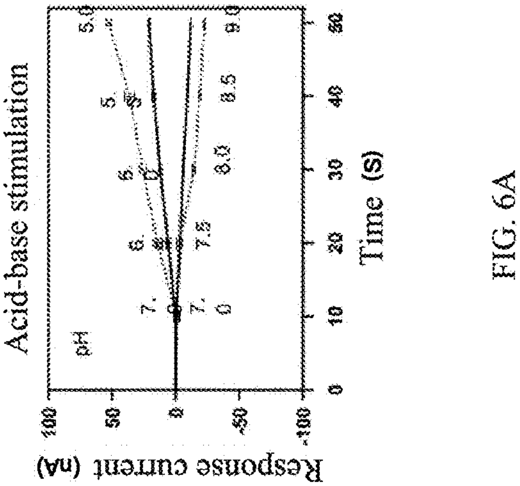

The test results obtained after the CSMA hydrogel treatment, as shown in FIGS. 6A, 6B, and 6C, are similar to those of the PQ-10 gel treatment.

Example 23

Through electrochemical detection, the PQ-10 cationic hydrogel and the CSMA cationic hydrogel prepared in Example 2 and Example 3 were used to assess the desensitizing effects of the cationic materials on a dentin hypersensitivity model of a living animal.

1) A dentin hypersensitivity model was constructed on a mandibular molar of an experimental animal (miniature pig). Of the measurement electrodes of a picoammeter, the positive electrode was placed in the electrolytic cell, and the negative electrode was placed in the dental pulp chamber.

Under an external voltage of 0 V, pressure stimuli (100, 200, 300, and 400 mmHg), acid-base stimuli (pH=5, 5.5, 6, 6.5, 7.5, 8, 8.5, and 9), and cold-hot stimuli (5° C., 13° C., 21° C., 29° C., 45° C., 53° C., 61° C., and 69° C.) were applied to the electrolyte solution (physiological saline) in the electrolytic cell, and the resulting changes in electric current on the hypersensitivity model were detected.

2) On the dentin hypersensitivity model of the animal, the value of the forward current induced by the strongest acid stimulus was approximately 55.49 nA, which decreased to 30.48 nA after the gel treatment. The value of the reverse current induced by the strongest base stimulus was approximately −33.15 nA, which decreased to −15.72 nA after the PQ-10 gel treatment.

3) On the dentin hypersensitivity model of the animal, the value of the forward current induced by the strongest cold stimulus was approximately 556 nA, which decreased to 238.74 nA after the gel treatment. The value of the reverse current induced by the strongest hot stimulus was approximately −551.32 nA, which decreased to −235.42 nA after the PQ-10 gel treatment.

4) On the dentin hypersensitivity model of the animal, the value of the forward current induced by the strongest pressure stimulus was approximately 44.26 nA, which decreased to 25.84 nA after the PQ-10 gel treatment.

Figures 5D, 5E, 5F:
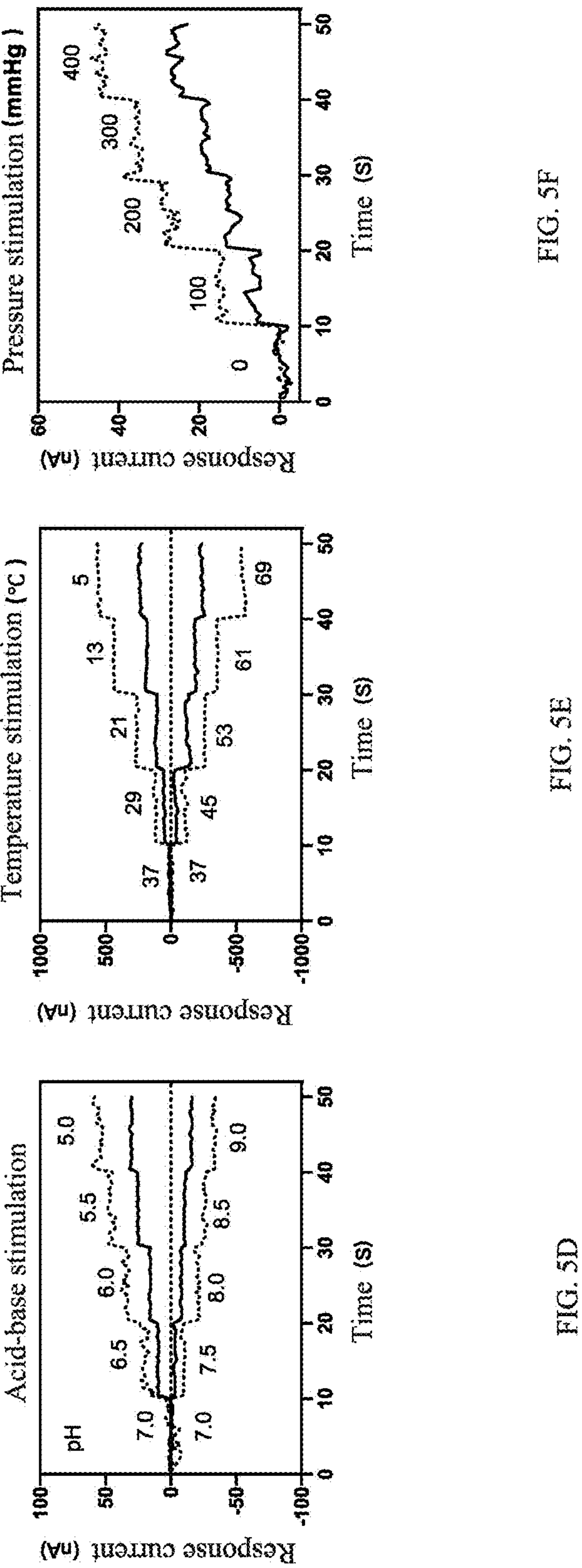

The results of the PQ-10 gel treatment on the extracted tooth are shown in FIGS. 5D, 5E and 5F.

Figure 6F:
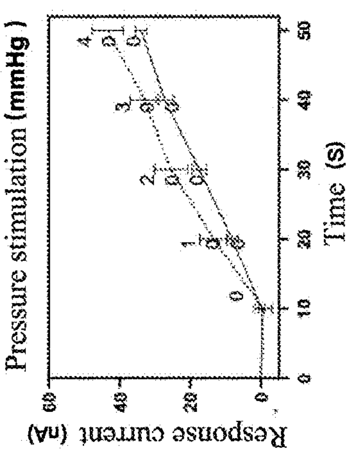
Figure 6F:
Figure 6E:
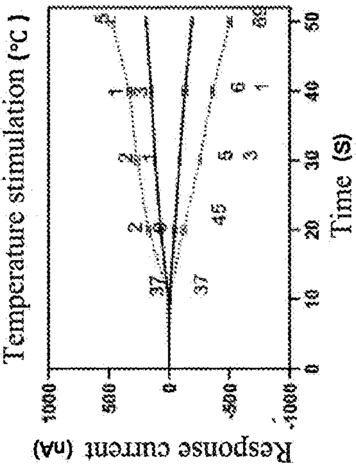
Figure 6D:
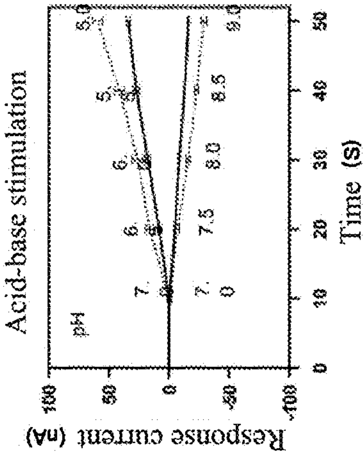

The test results obtained after the CSMA hydrogel treatment, as shown in FIGS. 6D, 6E, and 6F, are similar to those of the PQ-10 gel treatment.

Example 24

Through electrophysiological detection, the PQ-10 cationic hydrogel and the CSMA cationic hydrogel prepared in Example 2 and Example 3 were used to assess the desensitizing effects of the cationic materials on a dentin hypersensitivity model of a living animal.

1) On a dentin hypersensitivity model of a living animal, approximately 2 cm of the trunk of the mandibular nerve that controls the sensation of the mandibular molars was separated by dissection, and the measurement electrodes of the electrophysiological detection equipment were placed on the trunk of the mandibular nerve. The action potential changes in the trunk of the mandibular nerve when various types of stimuli were applied to the dentin hypersensitivity model were detected.

2) The amplitude of the action potential induced by acid stimuli was approximately 0.4 mV, which decreased to 0.15 mV after the gel treatment; the amplitude of the action potential induced by base stimuli was approximately 0.3 mV, which decreased to 0.1 mV after the gel treatment.

3) The amplitude of the action potential induced by cold stimuli was approximately 0.7 mV, which decreased to 0.3 mV after the gel treatment; the amplitude of the action potential induced by hot stimuli was approximately 0.5 mV, which decreased to 0.2 mV after the gel treatment.

4) The amplitude of the action potential induced by pressure stimuli was approximately 0.3 mV, which decreased to 0.15 mV after the gel treatment.

Figure 7:
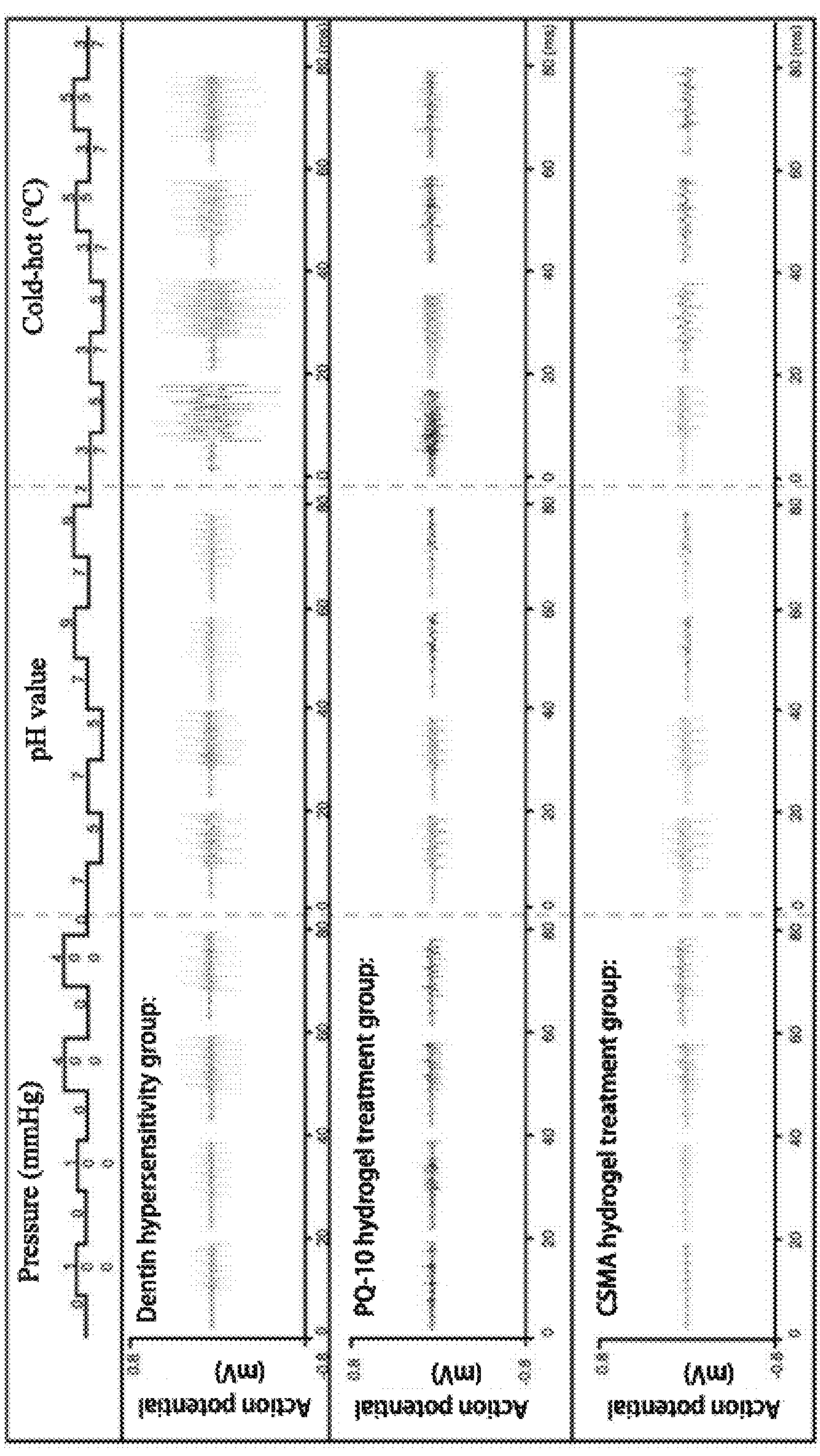
FIG. 7 shows the electrophysiological test results of the dentin hypersensitivity model of a living animal.

The desensitizing treatment effectiveness assessed by electrophysiological detection is shown in FIG. 7.

Example 25

Clinical desensitization experiments were adopted. The PQ-10 cationic hydrogel and the CSMA cationic hydrogel prepared in Example 2 and Example 3 were used to assess the desensitizing effects of the cationic materials in clinical trials.

20 hypersensitive teeth from patients with dentin hypersensitivity were included for the comparison of the VAS scores assessed before, immediately after, and in a follow-up examination 3 months after the treatment with the PQ-10 hydrogel, and those with the CSMA hydrogel. It can be observed that the cationic hydrogels had a better desensitizing effect and longer lasting effectiveness.

Figure 8A:
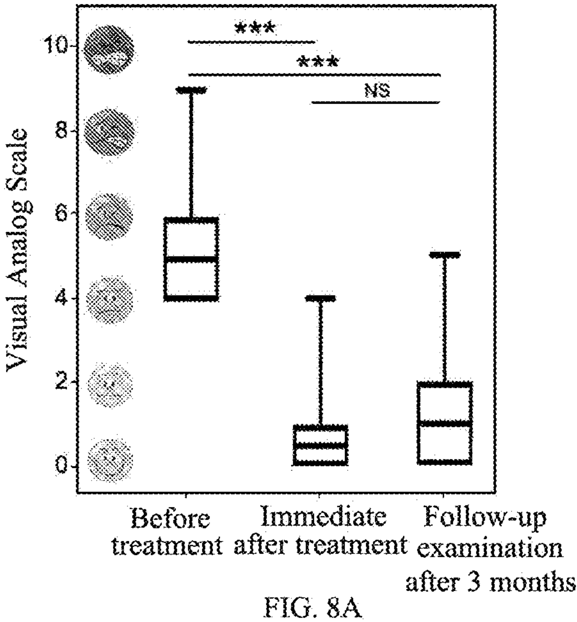
FIG. 8A is a diagram showing the results of the clinical desensitization experiments using the cationic hydrogel (polyquaternium-10 hydrogel).
Figure 8B:
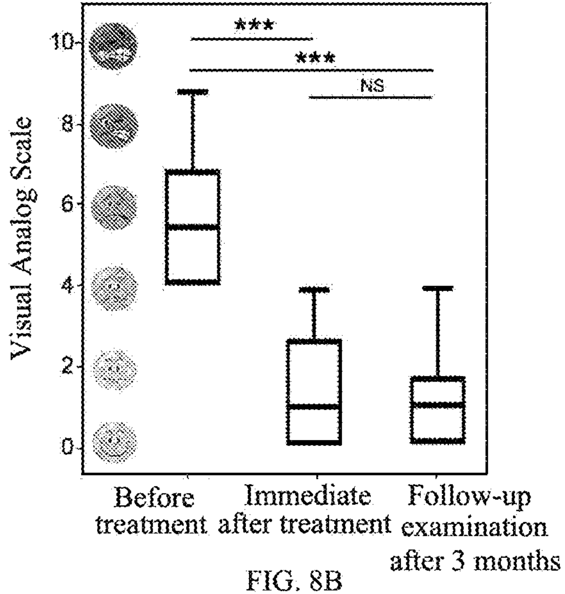
FIG. 8B is a diagram showing the results of the clinical desensitization experiments using the cationic hydrogel (methacrylated chitosan hydrogel).

The results of the desensitizing treatment effect with the PQ-10 hydrogel are shown in FIG. 8A. The results of the desensitizing treatment effect with the CSMA hydrogel are shown in FIG. 8B.

However, the above-mentioned are only specific examples of the present disclosure, and should not be used to limit the scope to implement the present disclosure. Therefore, the replacement of equivalent components, or equivalent changes and modifications made in accordance with the patent protection scope intended by the present disclosure, should still fall within the scope of the appended claims of the present disclosure.

What is claimed is:

1. A method of using a cationic material for dental desensitization in oral materials to reduce action potential of the trunk of mandibular nerve, comprising applying the cationic material to a surface of a tooth or tooth coverings of a subject in need, wherein the cationic material comprises a polyquaternium-10 hydrogel, the polyquaternium-10 has a molecular weight of 100 to 5000 kDa and a charge density of 0.0001 to 0.002 eq/g and a nitrogen content of 0.5 to 2.5 wt %, and the mass concentration of the polyquaternium-10 in the hydrogel is 0.1% to 10%, wherein the polyquaternium-10 hydrogel is prepared according to a method comprising the following steps:

step (1) dispersing hydroxyethyl cellulose in deionized water, stirring and dissolving uniformly, adding sodium hydroxide and 2,3-epoxypropyltrimethylammonium chloride respectively, and letting them react to obtain a reaction mixture;

step (2) neutralizing the reaction mixture obtained in the step (1) with hydrochloric acid, and then performing dialysis and freeze-drying to obtain the polyquaternium-10;

step (3) preparing the polyquaternium-10 obtained in the step (2) into the polyquaternium-10 hydrogel with the mass concentration of 0.1% to 10%.

2. The method of using the cationic material for dental desensitization in oral materials to reduce action potential of the trunk of mandibular nerve according to claim 1, wherein the step (1) is carried out with stirring at 30° C. to 95° C. for 0.5 to 24 hours; and in the step (3), the polyquaternium-10 obtained in the step (2) is slowly added into rapidly stirred deionized water, the temperature is raised to 30° C. to 95° C. to accelerate the swelling rate of the polyquaternium-10, and after 0.5 to 24 hours, a uniform and transparent solution is formed, so that the polyquaternium-10 hydrogel is prepared.

3. The method of using the cationic material for dental desensitization in oral materials to reduce action potential of the trunk of mandibular nerve according to claim 1, wherein the cationic material is formulated into a toothpaste.

4. The method of using the cationic material for dental desensitization in oral materials to reduce action potential of the trunk of mandibular nerve according to claim 1, wherein the cationic material is applied to coat the surface of the tooth coverings, and the method further comprises applying, a backing film layer onto the cationic material.

5. The method of using the cationic material for dental desensitization in oral materials to reduce action potential of the trunk of mandibular nerve according to claim 4, wherein the tooth coverings are selected from the group consisting of dental braces, dental adhesives, retainers, dental patches, and chewing gum; and the backing film layer is selected from one or more of EVA films, PLA films, and PVA films.

* * * * *